US010357148B2

(12) United States Patent
Ramsey

(10) Patent No.: US 10,357,148 B2
(45) Date of Patent: Jul. 23, 2019

(54) CONTAINER

(71) Applicant: Meditech Endoscopy Limited, Chesterfield (GB)

(72) Inventor: Peter Ramsey, Chesterfield (GB)

(73) Assignee: MEDITECH ENDOSCOPY LIMITED (GB)

( * ) Notice: Subject to any disclaimer, the term of this patent is extended or adjusted under 35 U.S.C. 154(b) by 779 days.

(21) Appl. No.: 14/785,682

(22) PCT Filed: Dec. 20, 2013

(86) PCT No.: PCT/GB2013/053382
§ 371 (c)(1),
(2) Date: Oct. 20, 2015

(87) PCT Pub. No.: WO2014/177822
PCT Pub. Date: Nov. 6, 2014

(65) Prior Publication Data
US 2016/0073867 A1 Mar. 17, 2016

(30) Foreign Application Priority Data

Apr. 30, 2013 (GB) .................................. 1307793.8
Jul. 31, 2013 (GB) .................................. 1313698.1

(51) Int. Cl.
A61B 1/12 (2006.01)
B65D 25/48 (2006.01)
(Continued)

(52) U.S. Cl.
CPC .......... A61B 1/126 (2013.01); A61B 1/00119 (2013.01); A61B 1/00128 (2013.01);
(Continued)

(58) Field of Classification Search
CPC ... B65D 25/48; Y10T 137/86348; A61B 1/12; A61B 1/015; A61B 1/125; A61B 1/126;
(Continued)

(56) References Cited

U.S. PATENT DOCUMENTS 4,261,343 A * 4/1981 Ouchi .................... A61B 1/12
600/158
5,794,824 A 8/1998 Jeong
(Continued)

FOREIGN PATENT DOCUMENTS

EP 2017195 A1 1/2009
JP S5911828 A 1/1984
(Continued)

Primary Examiner — Atif H Chaudry
(74) Attorney, Agent, or Firm — Hayes Soloway PC

(57) ABSTRACT

This invention relates to a container for use with an endoscope. More particularly, this invention relates to a container for storing and delivering sterile water to an endoscope. A container for storing sterile water for supply to an endoscope comprises a substantially rigid receptacle providing an internal volume for storing said water, the receptacle having opposing first and second end walls, in use said first end wall forming a base of the receptacle and said second end wall forming a top of the receptacle such that a vertical axis of the receptacle extends substantially perpendicular to the first and second end walls; a first port for connection to an air line of an endoscope; a second port for connection to a water line of an endoscope; a first fluid conduit extending between the receptacle and the first port; and a second fluid conduit extending between the receptacle and the second port, wherein, in use, the first and second ports are located in a fixed position with respect to the receptacle such that the first and second ports lie in the same vertical plane as the centre of gravity of the container when the receptacle is filled with water.

17 Claims, 9 Drawing Sheets

(51) Int. Cl.
*A61B 1/015* (2006.01)
*A61B 1/00* (2006.01)
*G02B 23/24* (2006.01)
*A61B 19/00* (2006.01)

(52) U.S. Cl.
CPC .......... *A61B 1/00131* (2013.01); *A61B 1/015* (2013.01); *A61B 1/12* (2013.01); *A61B 1/125* (2013.01); *B65D 25/48* (2013.01); *G02B 23/2476* (2013.01); *A61B 2019/343* (2013.01); *Y10T 137/86332* (2015.04); *Y10T 137/86348* (2015.04)

(58) Field of Classification Search
CPC ............ A61B 1/00119; A61B 1/00128; A61B 1/00131
See application file for complete search history.

(56) References Cited

U.S. PATENT DOCUMENTS

| | | | |
|---|---|---|---|
| 6,210,322 | B1 | 4/2001 | Byrne |
| 6,485,412 | B1 | 11/2002 | Byrne |
| 2003/0032862 | A1* | 2/2003 | Ota .................... A61B 1/00068 600/158 |
| 2003/0045779 | A1 | 3/2003 | Ito |
| 2009/0209822 | A1 | 8/2009 | Ikeda |
| 2012/0091092 | A1 | 4/2012 | Adams et al. |

FOREIGN PATENT DOCUMENTS

| | | |
|---|---|---|
| JP | H03258233 A | 11/1991 |
| JP | 2006325813 A | 12/2006 |
| WO | 2007138350 A1 | 12/2007 |
| WO | 2008122969 A1 | 10/2008 |

* cited by examiner

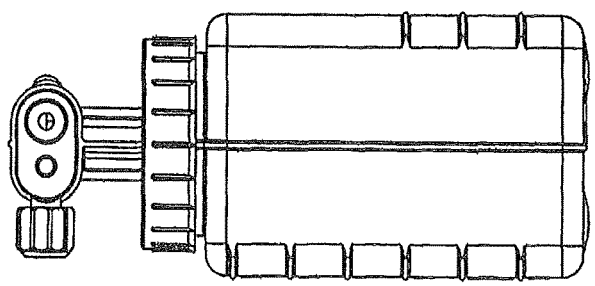
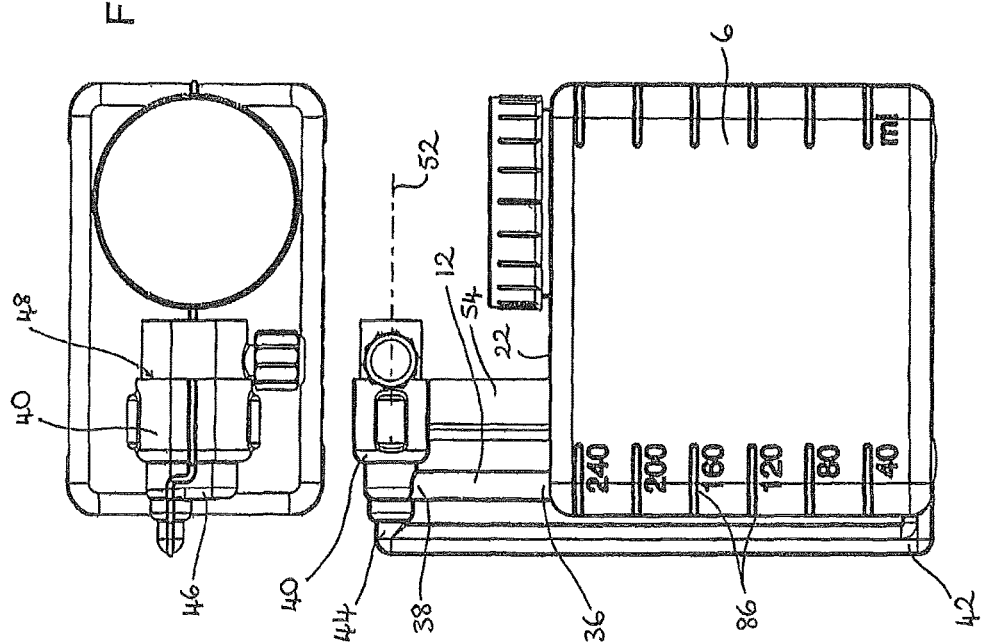
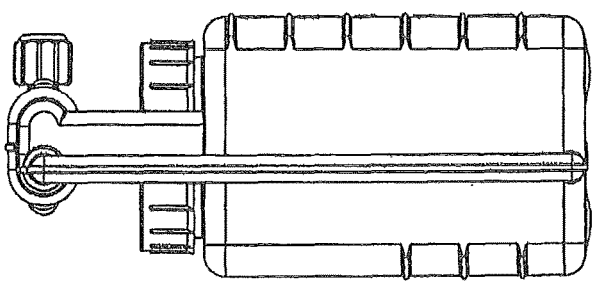

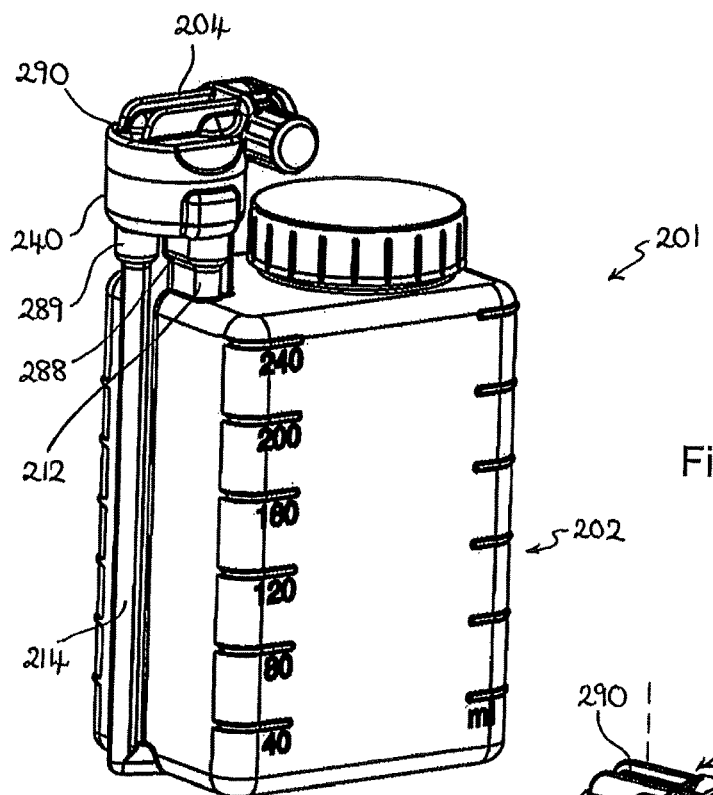
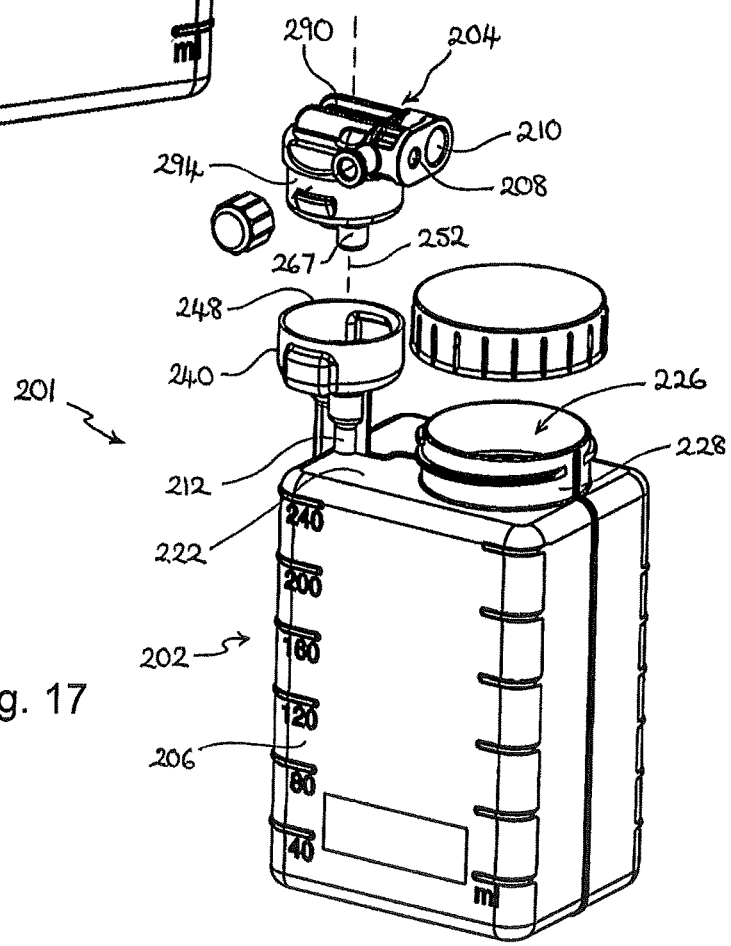
Fig. 16
Fig. 17

CONTAINER

BACKGROUND a. Field of the Invention

This invention relates to a container for use with an endoscope. More particularly, this invention relates to a container for storing and delivering sterile water to an endoscope.

b. Related Art

Endoscopes are commonly used to provide an internal view of a human or animal body, in particular, views of body cavities. Accordingly, endoscopes typically comprise a flexible tube that is inserted into the body. A lens system housed within the flexible tube transmits images from a distal lens at the tip of the tube back to an eyepiece or image sensor at the other end of the tube, to allow an operator to see the internal surfaces and spaces of interest within the body.

Endoscopes generally also include one or more channels through which instruments may be inserted to enable procedures, such as biopsies, to be carried out proximate the tip of the endoscope. These channels also permit fluids including liquids and gasses such as water, air and carbon dioxide, to be delivered through the endoscope. These fluids may be used for irrigation, insufflation or for other purposes, such as rinsing.

It is common during endoscopic procedures for particulate matter present within the body cavity to build up on the lens at the distal end of the endoscope. It is, therefore, necessary to be able to rinse the lens during the procedure to provide an uncompromised view for the operator. This is usually achieved by directing a supply of sterile water across the tip of the endoscope.

Typically, the sterile water is supplied from a separate water bottle that is removeably attached to the endoscope by means of flexible tubing, as illustrated in FIG. 15. When the operator wishes to flush the endoscope with water, a button on the endoscope is depressed which directs a flow of air under pressure from the air supply line of the endoscope, through a first flexible tube and into the bottle. This air forces water from the bottle through a second flexible tube and into the water supply line of the endoscope. The water then flows along a channel within the endoscope and is directed across the outer surface of the distal lens to clean it.

Generally the water bottles are mounted at a distance from the endoscope and a relatively long length of flexible tubing connects the water bottle to the endoscope. The flexibility of the tubing means that it is easy to install and remove. Furthermore, having a relatively long length of tubing, in addition to its flexibility provides a tolerance as to where the bottle is positioned relative to the endoscope. It may be necessary in some instances for the bottle to be mounted further from the endoscope than in other instances.

Typically the water bottles contain enough sterile water to be used throughout several endoscopy procedures in a single day; however, the water bottle also provides means for permitting additional sterile water to be added to the bottle if necessary. At the end of the day the bottle and flexible tubing are removed for cleaning and sterilisation. The bottle is then refilled with sterile water the next time it is used.

A major disadvantage of this system is that the water bottle and tubing can become a source of cross-contamination if the bottle and tubing are not cleaned, disinfected, sterilized or dried correctly at the end of the day. If improperly reprocessed, the irrigation water bottle and tubing set can become colonized with *P. aeruginosa* and/or other bacteria during storage, which may then contaminate the sterile water added to the bottle for subsequent endoscopic procedures. Furthermore, there is significant expense, both in terms of time and money, associated with cleaning and sterilising the bottles and tubing used in these procedures.

A known system, designed to reduce the infection risks associated with cleaning and sterilisation, comprises a disposable water bottle cap and flexible tubing assembly. The cap is designed to be secured to a disposable water bottle containing sterile water and the tubing forms a fluid connection between the water bottle and the endoscope. Although these cap and flexible tube assemblies are disposable, they are still designed for 24 hour use and are arranged to be detached from and attached to multiple endoscopes during the day. The flexible tubing, therefore, has at an opposite end to the cap a connector having female air and water ports that connect to the male air and water ports of the endoscope. In this arrangement a first flexible tube extends between the air line of the endoscope and the cap, and a second flexible tube extends from the water line of the endoscope, through the cap and down towards the base of the water bottle. Water is then pumped from the bottle in a similar manner to that described above.

Additionally, it is known to provide a clip or clamp around the flexible tubing proximate the connector. This clip is used to clamp the tubing and minimise the backflow of fluid along the tubing, especially when an endoscope is being detached. The clip does not, however, completely prevent the capillary backflow of fluid into the length of tubing between the connector and the clip and, as such, there remains an infection risk with these systems, due to cross-contamination between endoscopic procedures.

It is, therefore, an object of the present invention to provide an improved means for supplying water to an endoscope that overcomes at least some of the disadvantages mentioned above.

SUMMARY OF THE INVENTION

According to a first aspect of the present invention there is provided a container for storing sterile water for supply to an endoscope, the container comprising:

a substantially rigid receptacle providing an internal volume for storing said water, the receptacle having opposing first and second end walls, in use said first end wall forming a base of the receptacle and said second end wall forming a top of the receptacle such that a vertical axis of the receptacle extends substantially perpendicular to the first and second end walls;

a first port for connection to an air line of an endoscope;

a second port for connection to a water line of an endoscope;

a first fluid conduit extending between the receptacle and the first port; and a second fluid conduit extending between the receptacle and the second port, wherein, in use, the first and second ports are located in a fixed position with respect to the receptacle such that the first and second ports lie in the same vertical plane as the centre of gravity of the container when the receptacle is filled with water.

The container of the present invention can, therefore, be connected directly to the endoscope and can be suspended from the endoscope. This means that it is not necessary to have means or space to support the container separately from the endoscope and it is not necessary to connect the receptacle to the endoscope by means of relatively long flexible tubing, as in prior art devices. By negating the need for tubing, the container of the present invention reduces the likelihood of cross-contamination.

Preferably the first and second fluid conduits are substantially rigid.

In preferred embodiments the first and second ports are located at a fixed distance above said top of the receptacle. In this position the receptacle is suspended below the endoscope when the container is connected to the endoscope.

The shape of the container is preferably such that the centre of gravity remains in the same vertical plane, independent of the volume of water within the container. Advantageously, therefore, because the first and second ports are located in the same vertical plane as the centre of gravity of the container, when the container is suspended by the ports, only a minimal twisting force is applied to the endoscope due to the weight of the container.

In some embodiments an outlet of the receptacle is located proximate the first end wall, providing a passage for said sterile water to exit said internal volume, and an inlet of the receptacle is located proximate the second end wall, providing a passage for gas to enter said internal volume. The first fluid conduit extends between said inlet and said first port and the second fluid conduit extends between said outlet and said second port.

Preferably the first and second conduits are integrally formed with the receptacle. This makes the container cheaper and easier to manufacture, as well as minimising the number of joints and connections in the container, which may otherwise be a cause of failure or a site of contamination of the container.

The first and second conduits may be provided external to the receptacle.

In preferred embodiments the container comprises a third port for connection to a source of gas and a third fluid conduit extending between the third port and the first fluid conduit. This enables a source of carbon dioxide to be connected to the container in circumstances in which, for example, it is preferable to use carbon dioxide rather than air during an endoscopy procedure.

In some embodiments it is desirable if the second end wall includes an opening for filling the receptacle with sterile water. In these embodiments the opening is preferably sealed with a cap. More preferably a distance between the first and second ports and the second end wall of the receptacle is such that, when the container is connected to an endoscope, the cap cannot be removed to provide access to the opening. In other embodiments it may be preferable if the container cannot be refilled such that the container is single use.

In preferred embodiments the container further comprises an adaptor socket and a connector configured to engage with said socket, the connector having opposing first and second ends. In these embodiments a first portion of the first fluid conduit extends between said inlet and the adaptor socket, and a first portion of the second fluid conduit extends between said outlet and the adaptor socket. Furthermore, the first and second ports are preferably provided in the first end of the connector, a second portion of the first fluid conduit is provided in the connector and extends between said first port and the second end of the connector; and a second portion of the second fluid conduit is provided in the connector and extends between said second port and the second end of the connector. The connector and adaptor socket are then preferably arranged such that when the connector is engaged in the adaptor socket said first and second portions of the first fluid conduit are in fluid communication such that a complete fluid flow path is formed between the first port and the inlet, and said first and second portions of the second fluid conduit are in fluid communication such that a complete fluid flow path is formed between the outlet and the second port.

Preferably the connector is made from an elastomeric material.

In embodiments of the container including a connector, an end of each of the first portions of the first and second fluid conduits preferably terminates at a counterbore, and an end of each of the second portions of the first and second fluid conduits preferably terminates at a spigot, each of the spigots being received in a corresponding one of the counterbores.

In some embodiments of the present invention the container comprises an aperture provided in the receptacle and a fluid conduit module comprising a substantially rigid main body. A first end of the main body comprises the first and second ports, and a second end of the main body is arranged to be engaged with and removed from the aperture of the receptacle. In these embodiments the first fluid conduit is formed in the main body and extends between the first port and the second end, and the second fluid conduit is formed in the main body and extends between the second port and the second end. Preferably the aperture is offset from said vertical axis of the receptacle.

Preferably the aperture is provided in the second end wall of the receptacle. Preferably the first and second ends of the main body of the fluid conduit module are substantially perpendicular to each other.

In particularly preferred embodiments the container comprises a third port for connection to a source of gas and a third fluid conduit extending between the third port and the first fluid conduit. This enables a source of carbon dioxide to be connected to the container in circumstances in which, for example, it is preferable to use carbon dioxide rather than air during an endoscopy procedure.

The receptacle may comprise a neck portion that extends around the aperture, and a flange that extends outwards around the main body of the fluid conduit module at a distance from the second end. The flange is preferably arranged to contact an upper edge of said neck when the second end of the main body is fully engaged with the aperture of the receptacle.

Preferably the container further comprises a collar for securing the fluid conduit module to the receptacle.

Preferably the fluid conduit module is made from an elastomeric material.

According to a second aspect of the present invention there is provided an assembly comprising a container for storing sterile water and an endoscope, the container being according to the first aspect of the present invention, and wherein the container is solely suspended from the endoscope. Preferably the receptacle of the container is suspended below the endoscope.

According to a third aspect of the present invention there is provided a container for storing sterile water for supply to an endoscope, the container comprising:
  a substantially rigid receptacle providing an internal volume for storing said water, the receptacle having opposing first and second end walls, in use said first end wall forming a base of the receptacle and said second end wall forming a top of the receptacle;
  an outlet of the receptacle located proximate the first end wall providing a passage for said sterile water to exit said internal volume;

an inlet of the receptacle located proximate the second end wall providing a passage for gas to enter said internal volume;

a first port for connection to an air line of an endoscope;

a second port for connection to a water line of an endoscope;

a first fluid conduit extending between said inlet and said first port; and a second fluid conduit extending between said outlet and said second port, wherein, said first and second conduits are substantially rigid.

Because the first and second conduits are substantially rigid, the container can be connected directly to the endoscope and can be suspended from the endoscope. This means that it is not necessary to have means or space to support the container separately from the endoscope and it is not necessary to connect the receptacle to the endoscope by means of relatively long flexible tubing, as in prior art devices. By negating the need for tubing, the container of the present invention reduces the likelihood of cross-contamination.

According to a fourth aspect of the present invention there is provided a container for storing sterile water for supply to an endoscope, the container comprising:

a substantially rigid receptacle providing an internal volume for storing said water, the receptacle having opposing first and second end walls, in use said first end wall forming a base of the receptacle and said second end wall forming a top of the receptacle such that a vertical axis of the receptacle extends substantially perpendicular to the first and second end walls;

an aperture provided in the receptacle;

a fluid conduit module comprising a substantially rigid main body, a first end of the main body including a first port for connection to an air line of an endoscope and a second port for connection to a water line of an endoscope, and a second end of the main body arranged to be engaged with and removed from the aperture of the receptacle;

a first fluid conduit formed in said main body and extending between said first port and the second end; and a second fluid conduit formed in said main body and extending between said second port and the second end, wherein, said aperture is offset from said vertical axis of the receptacle, and the first end lies in the same vertical plane as the centre of gravity of the container when the fluid conduit module is engaged with the receptacle and the receptacle is filled with water.

Because the receptacle and the fluid conduit module are substantially rigid, the container can be connected directly to the endoscope and can be suspended from the endoscope. This means that it is not necessary to have means or space to support the container separately from the endoscope and it is not necessary to connect the receptacle to the endoscope by means of relatively long flexible tubing, as in prior art devices. By negating the need for tubing, the container of the present invention reduces the likelihood of cross-contamination.

According to a fifth aspect of the present invention there is provided an assembly comprising a container for storing sterile water and an endoscope, the container being according to the third or fourth aspect of the present invention, and wherein the container is solely suspended from the endoscope. Preferably the receptacle of the container is suspended below the endoscope.

BRIEF DESCRIPTION OF THE DRAWINGS

The invention will now be further described by way of example only and with reference to the accompanying drawings, in which:

FIG. 10 is a plan view from above of the container of FIG. 1;

FIG. 11 is a plan view from a first end of the container of FIG. 1;

FIG. 12 is a plan view from the side of the container of FIG. 1;

FIG. 13 is a plan view from a second end of the container of FIG. 1;

FIG. 16 is a perspective view of a container for sterile water, including a main body and a connector, according to a third preferred embodiment of the present invention;

FIG. 17 is an exploded view of the container of FIG. 16;

DETAILED DESCRIPTION

It will be understood that references in the following description to top, bottom, upper, lower and other relative positional terms, refer to the position or orientation of features when the container, of the present invention, is in use.

Figure 1:
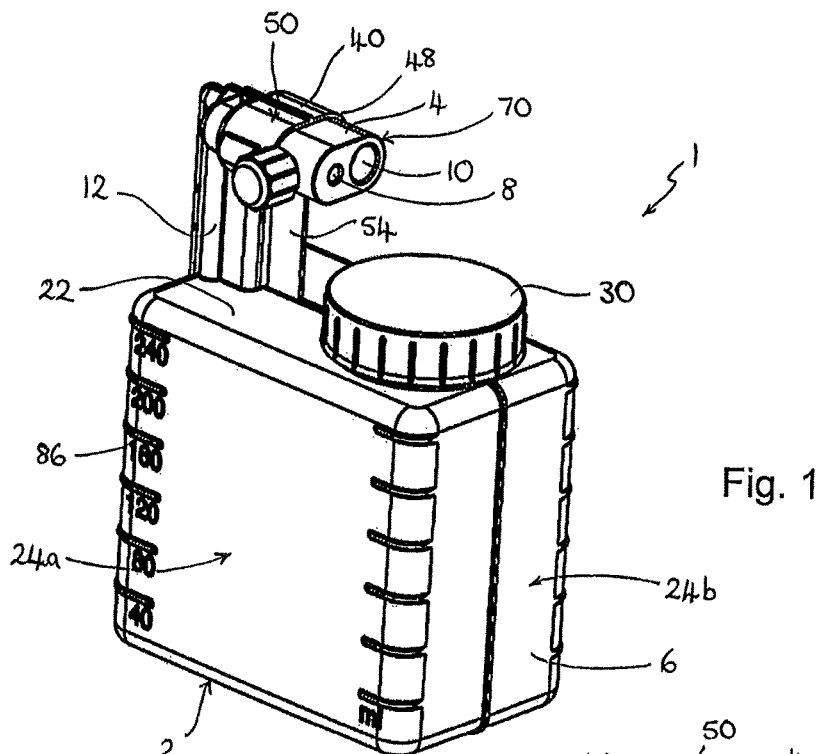
FIG. 1 is a perspective view of a container for sterile water according to a first preferred embodiment of the present invention showing, in particular, part of a connector providing ports permitting connection of the container to an endoscope.
Figure 2:
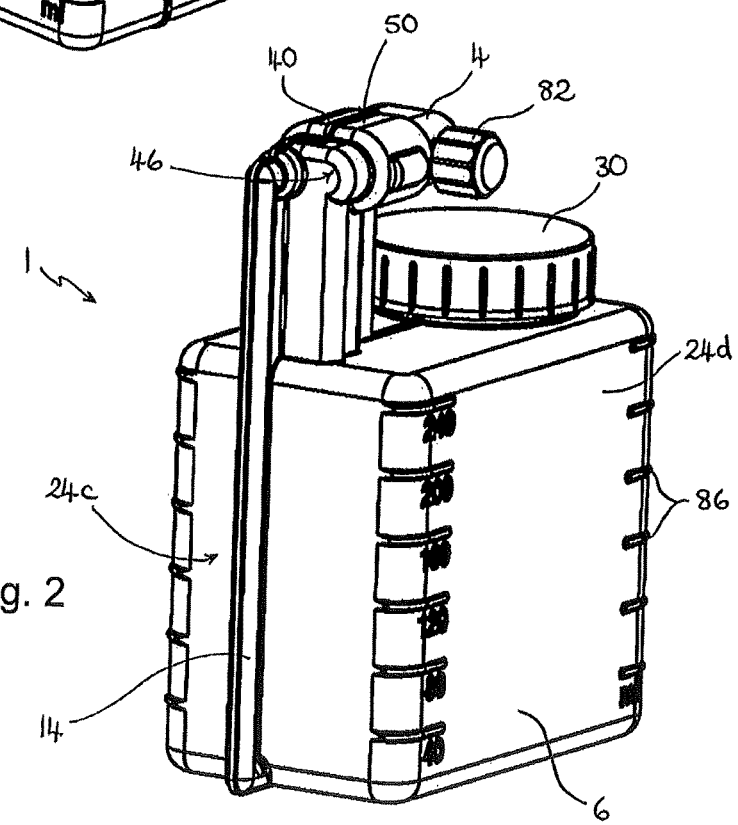
FIG. 2 is a perspective view of the container of FIG. 1 showing, in particular, an integral fluid conduit for water.
Figure 3:
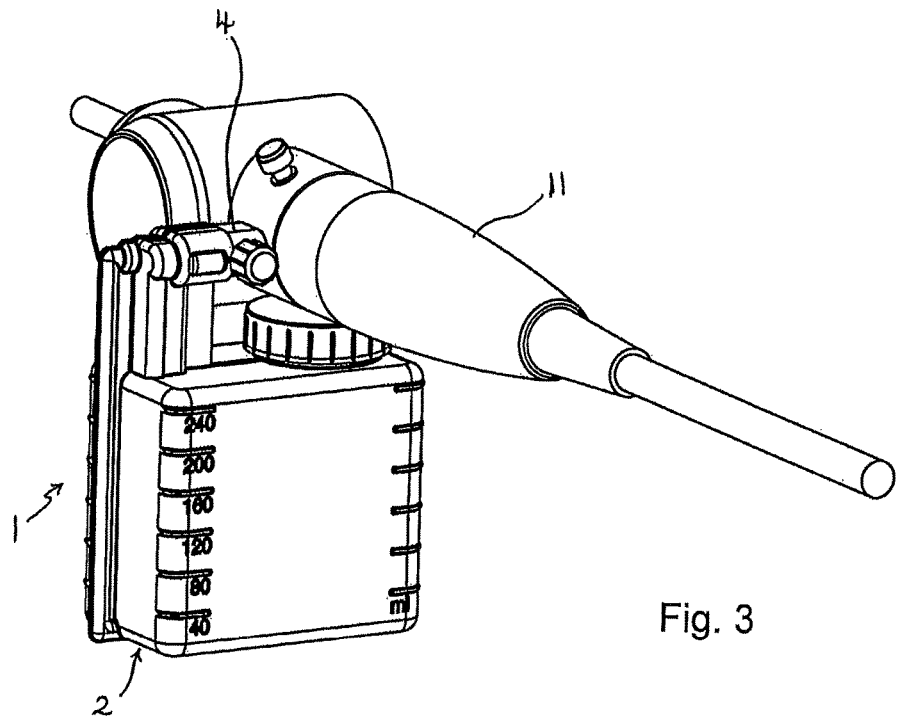
FIG. 3 is a perspective view of the container of FIG. 1 connected to an endoscope.

FIGS. 1 to 3 and FIGS. 7 to 13 show a container 1 according to a first preferred embodiment of the present invention. The container 1 is arranged to be directly connected to an endoscope 11, as shown in FIG. 3, to provide a supply of sterile water to the endoscope 11. Unlike prior art sterile water supply means, the container 1 does not require flexible tubing to connect to the endoscope, thereby reducing the possibility and likelihood of cross-contamination.

The container 1 comprises a main body 2 and a connector or fluid conduit module 4. The main body 2 comprises a substantially rigid receptacle 6 having an internal volume for holding a liquid such as sterile water, as shown most clearly in FIGS. 8 and 9. The connector 4 of the container 1 provides a female air port 8 and a female water port 10 for connection to, respectively, male air and water connectors or ports (not shown) on the endoscope 11 that are in fluid connection with the air and water lines of the endoscope 11, as understood by a person of skill in the art. The ports 8, 10 are connected to the internal volume of the receptacle 6 by means of fluid conduits 12, 14. A first fluid conduit 12 provides a passageway for air between the air port 8 and an inlet 16 in an upper region of the receptacle 6, and a second fluid conduit 14 provides a passageway for water between an outlet 18 in a lower region of the receptacle 6 and the water port 10.

In use, when an operator of the endoscope 11 requires a flow of sterile water through the endoscope 11, air is introduced, under pressure, into the container 1 from the air line of the endoscope 11, which is connected to the air port 8. The air passes along the first fluid conduit 12 and enters the upper region of the receptacle 6. Due to the rigidity of the receptacle 6, water held within the receptacle 6 is thereby forced or 'pumped' out though the outlet 18 of the receptacle 6. The water flows through the second fluid conduit 14 and into the water line of the endoscope 11 via the water port 10.

The receptacle 6 has a first end wall or base 20 and an opposing second end wall or top 22. In this embodiment the receptacle 6 is substantially cuboidal and, as such, four side walls 24a-d extend between the base 20 and top 22, thereby defining the internal volume of the receptacle 6. An opening 26 is provided in the top 22 of the receptacle 6 to allow the internal volume to be filled with sterile water. In this embodiment a neck 28 extends upwards around the opening 26. The opening 26 is sealed by means of a separate cap 30, and complementary external and internal screw threads are provided on the neck 28 and cap 30 respectively, to enable the cap 30 to be secured to the receptacle 6 and form a fluid-tight seal.

It will be appreciated that in other embodiments the container may be sealed such that additional sterile water cannot be added to the receptacle. This means that once all of the sterile water within the container has been used, the container must be removed from the endoscope and disposed of. This removes the possibility of contamination of the water during refilling of the container. In these embodiments, the container will be pre-filled with sterile water in a factory or packing plant, rather than being filled with sterile water at the site of the endoscopic procedures.

In further embodiments the cap 30 may be designed such that once the receptacle 6 has been filled with water and the cap 30 has been attached to the neck 28 around the opening 26, the cap 30 cannot subsequently be removed without breaking the cap 30 or a part of the main body 2. This renders the container 1 single use, but means that the container 1 does not have to be pre-filled with water at a factory or packing plant, thereby decreasing the weight of the containers 1 being transported and reducing the associated costs.

Figure 8:
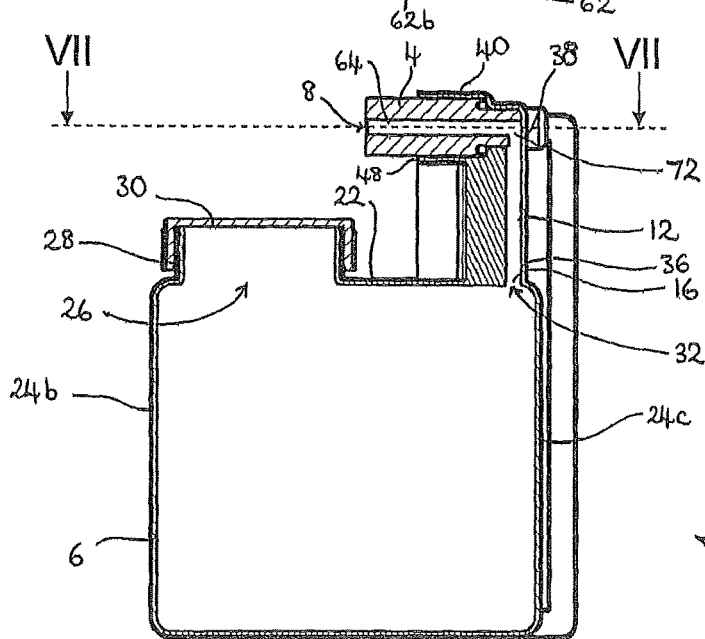
FIG. 8 is a cross-sectional view of the container of FIG. 1 along line VIII-VIII in FIG. 7.
Figure 9:
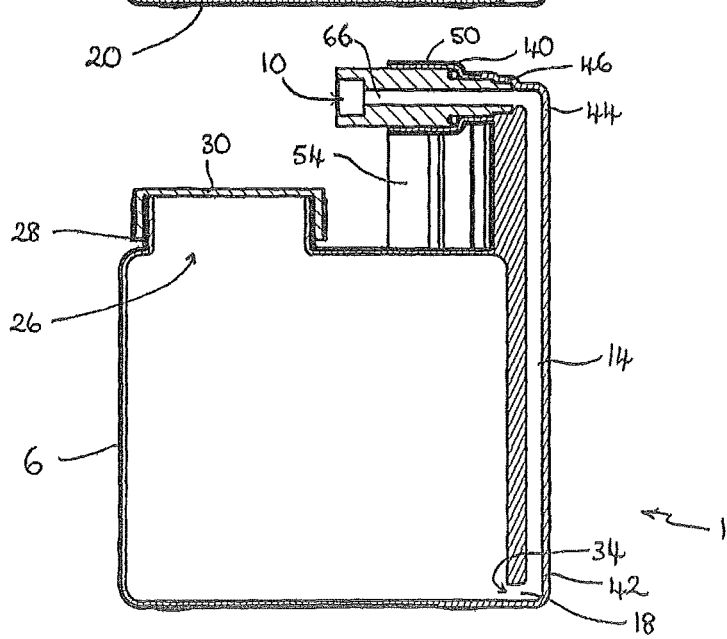
FIG. 9 is a cross-sectional view of the container of FIG. 1 along the line IX-IX in FIG. 7.

As shown most clearly in FIGS. 8 and 9, a first aperture 32 forms the inlet 16 in the top 22 of the receptacle 6, and a second aperture 34 forms the outlet 18 proximate the base 20 of the receptacle 6. In this example the outlet aperture 34 is formed in one of the side walls 24c. The outlet aperture 34 is preferably formed as close to the base 20 as possible to ensure that all of the water held within the receptacle 6 of the container 1 is able to drain through the outlet 18 and none of the water remains unusable in the bottom of the receptacle 6 below the level of the outlet 18. In some embodiments of the container, the outlet aperture 34 may be provided in the base 20 of the receptacle 6.

The main body 2 further comprises the first fluid conduit 12 and the second fluid conduit 14. The first and second fluid conduits 12, 14 are both substantially rigid and are preferably made of the same material as the receptacle 6. In preferred embodiments the receptacle 6 and conduits 12, 14 are made from a substantially rigid plastics material such as polyethylene or polypropylene, most preferably high density polyethylene (HDPE).

The first fluid conduit 12 extends between the receptacle 6 and the connector 4, terminating at a first end 36 at the inlet aperture 32 and at a second end 38 at an adaptor socket 40. The first fluid conduit 12 extends away from the top 22 of the receptacle 6 in a direction substantially perpendicular to the top 22, such that the adaptor socket 40 is located above the top 22 of the receptacle 6.

The second fluid conduit 14 also extends between the receptacle 6 and the adaptor socket 40, and terminates at a first end 42 at the outlet aperture 34. A first portion of the conduit 14 extends substantially perpendicularly away from the side wall 24c and a second portion of the conduit 14 then extends substantially parallel to the side wall 24c in a direction towards the top 22 of the receptacle 6. The conduit 14 terminates at a second end 44 at the adaptor socket 40.

This arrangement of the first and second fluid conduits 12, 14 means that the first fluid conduit 12 is substantially shorter in length than the second fluid conduit 14.

The adaptor socket 40 is arranged to receive and engage with the connector 4. The socket 40 comprises a closed end 46, an opposing open end 48 and a side wall 50 that extends axially between the closed and open ends 46, 48. The socket 40 is oriented such that a longitudinal or insertion axis 52 of the socket 40 (FIG. 12) extends substantially parallel to the top 22 of the receptacle 6. In addition to the socket 40 being supported by the conduits 12, 14, the socket 40 is further supported above the top 22 of the receptacle 6 by a strengthening rib 54 that extends between, at a first end of the rib 54, an outer surface of the socket 40 and, at a second end of the rib 54, an opposing outer surface of the top 22 of the receptacle 6. A side edge of the rib 54 extends in contact with an outer surface of a part of the first fluid conduit 12 between the top 22 of the receptacle 6 and the socket 40.

Advantageously, in this embodiment, the receptacle 6, the first and second conduits 12, 14, the socket 40 and the rib 54 are integrally formed, such that the main body 2 is a unitary part of the container 1. In other embodiments the conduits 12, 14 may be formed separately and subsequently joined to the receptacle 6 to form the main body 2 of the container 1. In these embodiments, however, the joints between the conduits 12, 14 and the receptacle 6 may provide potential areas of contamination or failure in the container 1 and, as such, it is preferable if at least the main body 2 of the container 1 is a single, unitary element.

Figure 4:
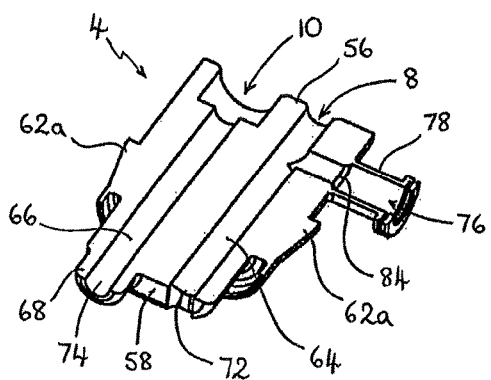
FIG. 4 is a sectional view of the connector of FIG. 1 showing fluid channels through the connector.

In order to allow the container 1 to be used in conjunction with a number of different types of endoscope, for example endoscopes made by different manufacturers, a plurality of different connectors 4 may be supplied to engage with the socket 40 of the main body 2. Each of the connectors 4 has the required configuration of air and water ports 8, 10 for attachment to a specific type or make of endoscope. One connector 4, shown most clearly in FIGS. 4, 5 and 6, comprises air and water ports 8, 10 suitable for connection to an Olympus™ series endoscope. The connector 4 extends axially between opposing first and second ends 56, 58. The female air port 8 and the female water port 10 are formed in the first end 56 and the ports 8, 10 are dimensioned and positioned for connection to the corresponding male air and water ports (not shown) on the endoscope 11.

In some embodiments, sealing means are provided in the air and water ports 8, 10 to form fluid-tight seals between the container 1 and the air and water ports of the endoscope 11. In other embodiments, however, the connector 4 is made from a compliant elastomeric material, for example low density polyethylene (LDPE) or another thermoplastic elastomer, such that separate sealing means are not required. In these embodiments a seal is formed directly between the ports 8, 10 in the connector 4 and the corresponding male ports of the endoscope 11, due to the compliant material of the connector 4.

A rear portion 60 of the connector 4, proximate the second end 58, has an external shape that is complementary to the internal shape of the adaptor socket 40 of the main body 2. The external dimensions of the connector 4 in this rear portion 60 are such that there is a push fit or interference fit of the connector 4 into the socket 40.

Figure 5:
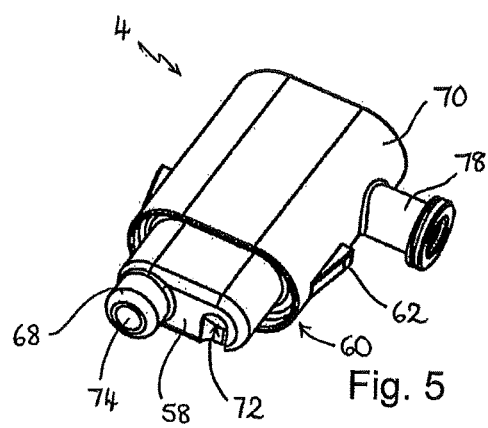
FIG. 5 is a perspective view of the connector of FIG. 1 showing, in particular, securing means for securing the connector within a socket of the container.
Figure 6:
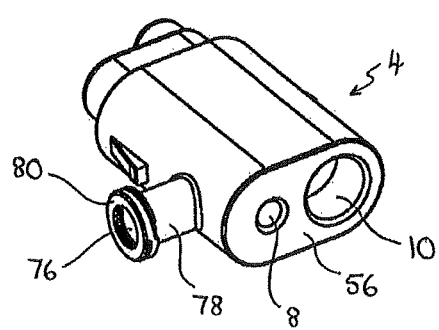
FIG. 6 is a perspective view of the connector of FIG. 5 showing the ports for connection to an endoscope.
Figure 7:
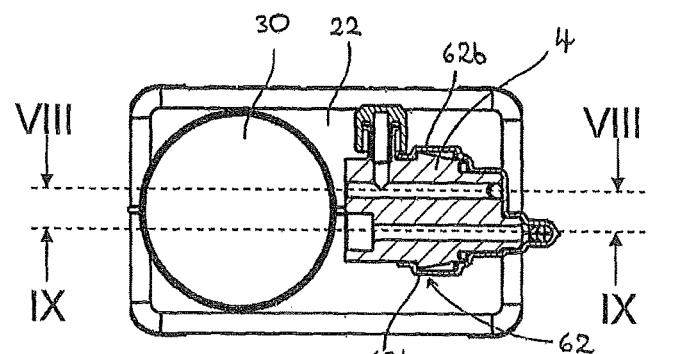
FIG. 7 is a cross-sectional view of the container of FIG. 1 along line VII-VII in FIG. 8.

As shown most clearly in FIGS. 5 and 7, the connector 4 and socket 40 further include retaining means 62. The retaining means 62 are arranged such that once the connector 4 has been inserted into the socket 40, it cannot subsequently be removed without damaging either the connector 4 or socket 40. This prevents the connector 4 accidentally being pulled out of the socket 40 and decreases the likelihood of contamination through interchanging of connectors 4.

In this example, the retaining means 62 are in the form of a pair of detents or projections 62a on the connector 4 and a corresponding pair of recesses 62b (FIG. 7) formed in the socket 40. The projections 62a have a generally triangular or barbed shape such that a sloped surface of each of the projections 62a enables the connector 4 to be pushed into the socket 40 in a first direction until the projections 62a engage in the recesses 62b, but does not allow the projections 62a to disengage from the recesses 62b when the connector 4 is pulled in an opposite, second direction. The retaining means 62, therefore, prevent the connector 4 being pulled out of the socket 40 when the container 1 is detached from the endoscope 11.

First and second fluid passageways 64, 66 extend through the connector 4 from each of the air and water ports 8, 10 respectively to the second end 58 of the connector 4. In this embodiment the second fluid passageway 66 terminates in an axially projecting spigot 68 at the second end 58 of the connector 4.

In use, the connector 4 is fully seated in the socket 40 such that the rear portion 60 of the connector 4 is within the socket 40 and a front portion 70 of the connector 4, proximate the first end 56, protrudes from the open end 48 of the socket 40. In this position, an end 72 of the first fluid passageway 64 in the connector 4 is aligned with the second end 38 of the first conduit 12 to form a complete and continuous first fluid flow path between the air port 8 and the inlet aperture 32 of the receptacle 6. Furthermore, the spigot 68 extends into the second end 44 of the second fluid conduit 14 such that an end 74 of the second fluid passageway 66 is aligned with the second end 44 of the second conduit 14, and a complete and continuous second fluid flow path is formed between the outlet aperture 34 of the receptacle 6 and the water port 10.

Because the connector 4 is made of a compliant elastomeric material and the dimensions of the connector 4 and socket 40 are such that there is a push fit between these two components, when the connector 4 is inserted into the socket 40 there is some compression of the material of the connector 4. This forms a gas tight seal around the passageways 64, 66 between the connector 4 and the socket 40, without the need for additional sealing means. In other embodiments in which the connector is not made of a compliant material, additional sealing means such as O-rings may be provided to form gas tight seals between the connector 4 and the socket 40.

In some circumstances it is preferable for carbon dioxide gas, rather than air, to be used during an endoscopic procedure, in particular for insufflation. In these situations, a main air pump connected to the endoscope 11 is switched off and a separate source of carbon dioxide gas is connected. It is, therefore, desirable if this carbon dioxide gas can also be used to pump the sterile water from the container 1, rather than requiring a further supply of air connected to the container 1.

In this embodiment the connector 4 comprises an auxiliary port 76 for connection to an additional source of gas, such as a source of carbon dioxide (not shown). The auxiliary port 76 comprises an inlet tube 78 that projects from the connector 4 in a direction perpendicular to the longitudinal or insertion axis of the connector 4. A distal end 80 of the inlet tube 78 is adapted for connection to a source of carbon dioxide as typically used in an endoscopy procedure. In particular, the distal end 80 comprises a part of a luer lock connector for connection to a hose of a supply of carbon dioxide (not shown). The distal end 80 of the inlet tube 78 is sealed with a suitable cap 82 when the container 1 is not connected to an auxiliary gas source.

The inlet tube 78 is located in the front portion 70 of the connector 4, proximate the first end 56, and the tube 78 is positioned such that a bore of the tube, or third fluid passageway 84, is in fluid communication with the first fluid passageway 64 in the connector 4.

By arranging the air port 8 and auxiliary port 76 in this way, it is only necessary to have two conduits 12, 14 in fluid connection with the receptacle 6; the first conduit 12 providing a passageway for the flow of air or carbon dioxide depending on the available gas source. This minimises the complexity of the container 1, further reducing the possibility of failure or contamination. Furthermore, the provision of an auxiliary port 76 means that the container 1 does not have to be disconnected from the endoscope 11 to allow a source of carbon dioxide to be connected to the container 1.

In use, when it is desired to use carbon dioxide during the endoscopy procedure in place of air, the air pump connected to the endoscope 11 is switched off, and a source of carbon dioxide gas is connected to the auxiliary port 76 of the container 1. Due to the configuration of the first and third passageways 64, 84 within the connector 4, the carbon dioxide gas flows along the third passageway 84 and then is able to flow both in a first direction along the first passageway 64 into the upper region of the receptacle 6 and also in a second direction along the first passageway 64 into the endoscope 11, via the air port 8. A valve arrangement in the endoscope 11 is then used to control the flow of carbon dioxide gas or water into the endoscope 11. In particular, with the valve in a first position carbon dioxide is able to flow from the container 1, through the air port 8 and into the endoscope 11. This flow of carbon dioxide may then be used for insufflation. In this first position the valve blocks the flow of water into the endoscope 11. With the valve in a second position, the air line of the endoscope 11, through which the carbon dioxide gas would flow, is blocked and the water line is open. The carbon dioxide gas, therefore, flows into the upper region of the receptacle 6 and forces water out of the receptacle 6, along the second fluid conduit 14 and into the water line of the endoscope 11.

It is to be noted that, when the container 1 is attached to the endoscope 11, the container 1 is supported solely by and at the connection between the female air and water ports 8, 10 of the container 1 and the male air and water ports of the endoscope 11. In this way, the receptacle 6 of the container 1 is suspended below the endoscope 11, as shown in FIG. 3. The container 1 of the present invention is, therefore, not supported by any other means and is solely suspended from the endoscope 11.

The dimensions of the connector 4 and socket 40 are designed such that the air and water ports 8, 10 lie directly above the centre of gravity of the container 1, i.e. the ports 8, 10 lie in the same vertical plane as the centre of gravity. Furthermore, the geometry of the container 1 is such that, as the amount of water within the receptacle varies, the centre of gravity shifts vertically but does not move horizontally. This arrangement means that, when the container 1 is connected to the endoscope 11, the receptacle 6 is suspended directly below the endoscope 11 and minimal twisting or bending forces are applied to the male air and water ports of the endoscope 11 due to the weight of the container 1.

Additionally, when the container 1 is attached to the endoscope 11, the distance between the endoscope 11 and the top 22 of the receptacle 6, and the position of the opening 26 and associated screw cap 30, are such that the screw cap 30 cannot be removed from the neck 28 around the opening 26 while the container 1 is attached to the endoscope 11. This prevents the receptacle 6 being opened while the container 1 is connected to an endoscope 11, thereby minimising the possibility of contamination of the sterile water within the container 1.

In this embodiment, the container 1 is designed to be used throughout the day during a number of endoscopic procedures. Accordingly, the container 1 is sized to hold approximately 250 ml of water within the receptacle 6. Preferably, the internal volume of the receptacle 6 is between 250 ml and 300 ml.

Figure 14:
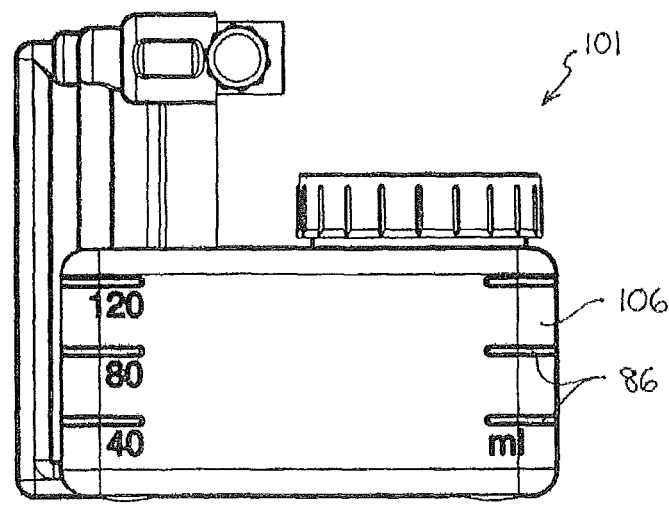
FIG. 14 is a plan view from the side of a container according to a second preferred embodiment of the present invention.
Figure 15:
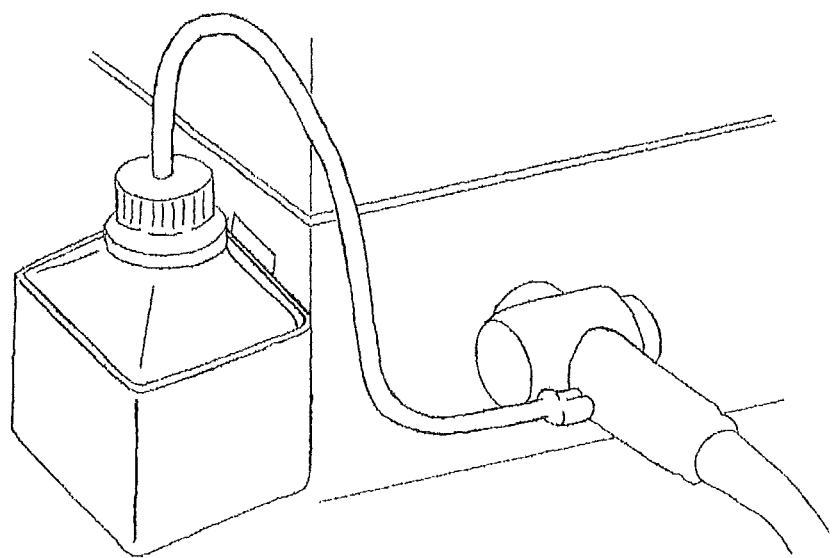
FIG. 15 shows a prior art water bottle connected to an endoscope via flexible tubing.

In other embodiments the container may be designed to only be used during a single endoscopic procedure, or only two or three procedures, and will, therefore, be sized to hold a smaller volume of water. FIG. 14 illustrates one such container 101. In this embodiment the receptacle 106 of the container 101 has an internal volume of between 125 ml and 150 ml and is designed to hold approximately 120 ml of sterile water. Only a depth of the receptacle 106 has been decreased, compared to the receptacle 6 of the first embodiment, and the other dimensions of the container 101 are the same as the equivalent dimensions of the container 1 of the first embodiment.

Ideally volume markings 86 are provided on the receptacle 6, 106 so that a user can see how much water is within the receptacle 6, 106. Preferably the volume markings 86 comprise a scale moulded into the receptacle 6, 106 or printed onto an outer surface of the receptacle 6, 106, and the receptacle 6, 106 is preferably made of a transparent or translucent material such that the water level can be seen against the scale. In particularly preferred embodiments a distance between the scale markings 86 corresponds to the typical volume of water used during a single endoscopy procedure, namely about 40 ml.

Figure 18:
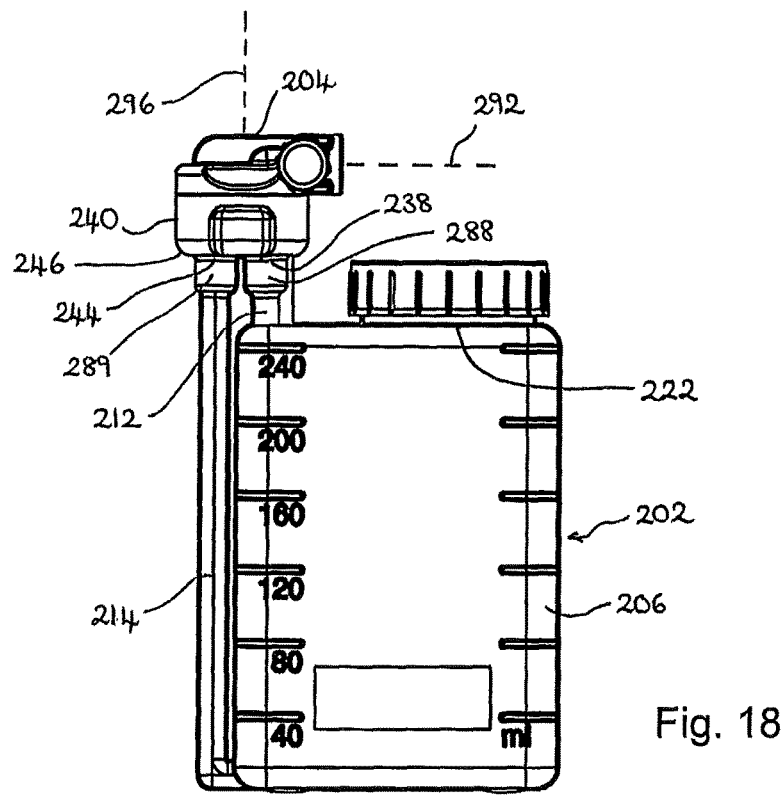
FIG. 18 is a side view of the container of FIG. 16.
Figure 19:
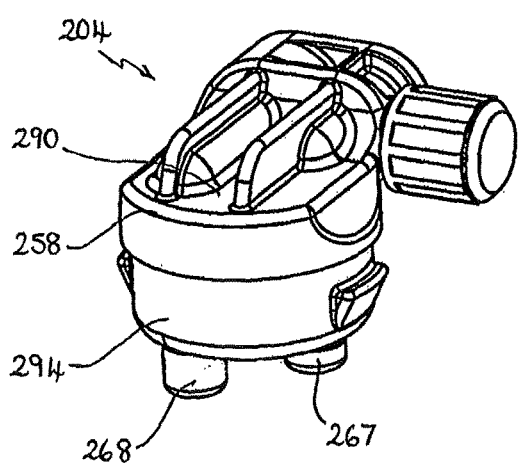
FIG. 19 is a perspective view from above of the connector of the container of FIG. 16.

FIGS. 16 to 18 show a container 201 according to a third preferred embodiment of the present invention. The container 201 is substantially the same as the container 1 of the first embodiment, except for the geometry and engagement of the connector 204 and socket 240.

In this example the socket 240 is oriented such that its open end 248 is uppermost and an insertion axis 252 of the socket 240 is substantially vertical. Both of the first and second conduits 212, 214 terminate at their respective second ends 238, 244 at the closed, lowermost end 246 of the socket 240. An end portion 288, 289 of each of the conduits 212, 214 at their second ends 238, 244 is enlarged to form a counterbore.

Orienting the socket 240 in this way with respect to the receptacle 206 means that the main body 202 of the container 201 may be more easily formed by blow moulding, whilst achieving the required dimensional tolerances. In a preferred method of manufacture of the main body 202, two steel cores are positioned in the blow moulding tool in locations corresponding to the opening 226 and the socket 240 of the final container 201. The steel cores are trapped by the two halves of the blow moulding tool as they close, as understood by a person of skill in the art. The steel cores ensure that the concentricity and dimensional accuracy of the counterbores guarantee a perfect seal between the main body 202 and the connector 204, as described below.

The blow moulding mould is preferably designed such that any gaps between faces of the mould halves (parting surfaces) and the steel cores reduce the plastics material to such a thin section that, when the mould is opened after forming, the scrap material or flash can be easily peeled away to produce a very smooth edge around both the neck 228 and the socket 240. This is advantageous because manually cutting or trimming the flash introduces the risk of producing swarf which is undesirable because small pieces of swarf may remain in the container 201 and then may subsequently block a channel within an endoscope when the container is used.

Figure 20:
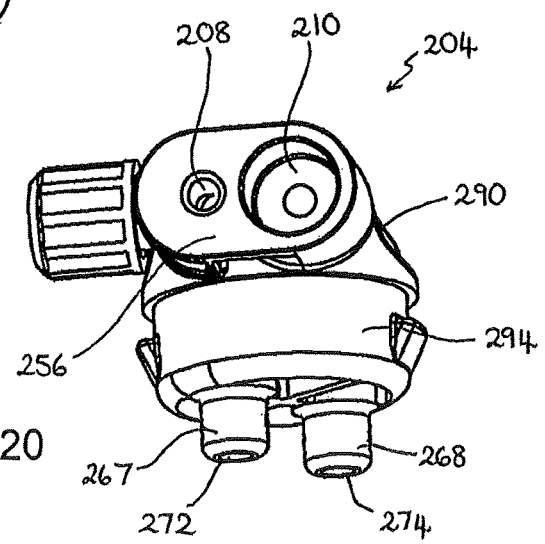
FIG. 20 is a perspective view from below of the connector of the container of FIG. 16

The connector 204 comprises female air and water ports 208, 210 in a first end 256 of the connector 204, as shown most clearly in FIG. 20. A first section of each of the first and second fluid passageways of the connector 204 extends through an upper region 290 of the connector 204 parallel to a first axis 292. The first axis 292 extends substantially parallel to the top 222 of the receptacle 206 when the connector 204 is in the socket 240 of the container 201. Proximate a second end 258 of the connector 204 the passageways turn through about 90° and a second section of each of the passageways extends through a lower region 294 of the connector 204. The second section of each of the passageways extends substantially parallel to a second, insertion axis 296 of the connector 204, which is substantially perpendicular to the first axis 292. Both the first and second passageways terminate at a second end 272, 274 in a projecting spigot 267, 268. The spigots 267, 268 project from the lower region 294 of the connector 204 in a direction substantially parallel to the insertion axis 296.

When the connector 204 is fully seated in the socket 240, the lower region 294 of the connector 204 is within the socket 240 and the upper region 290 of the connector 204 protrudes from the open end 248 of the socket 240. In this position, a first spigot 267 is received within the counterbore of the first fluid conduit 212 such that the end 272 of the first fluid passageway is aligned with the second end of the first conduit 212, and a complete and continuous first fluid flow path is formed between the air port 208 and the inlet aperture of the receptacle 206. A second spigot 268 is received within the counterbore of the second fluid conduit 214 such that the end 274 of the second fluid passageway 214 is aligned with the second end of the second conduit 214, and a complete and continuous second fluid flow path is formed between the outlet aperture of the receptacle 206 and the water port 210.

As in previous embodiments the connector 204 is preferably made from a compliant elastomeric material such as LDPE. The spigots 267, 268 are sized so that there is a push fit of the spigots 267, 268 into the corresponding counterbores. As the spigots 267, 268 are inserted, a slight compression of the elastomeric material causes a gas tight seal to be formed between the outer surfaces of the spigots 267, 268 of the connector 204 and the mating surfaces of the counterbores at the ends 238, 244 of the conduits 212, 214.

In some embodiments the outer surface of each of the spigots 267, 268 has a plain cylindrical form. In other embodiments, the outer surface of each of the spigots 267, 268 includes at least one circumferential, annular projection (not shown). When the spigots 267, 268 are inserted into the counterbores, it is this circumferential projection that forms the gas tight seal against the surface of the counterbore. In this way, the circumferential projections function like integrally formed O-rings around the spigots 267, 268.

In the preceding description the arrangement of the ports 8, 10, 208, 210 and receptacle 6, 106, 206 have been such that the container 1, 101, 201 is designed to be suspended underneath a part of the endoscope 11 when the container 1, 101, 201 is attached to the endoscope 11. This has the advantage that it is not necessary to incorporate valves, for example one way valves, into either the connector 4, 204 or the main body 2, 202 of the container 1, 101, 201.

In other embodiments, however, it may be preferable if the container is mounted such that the receptacle is above a part of the endoscope when the container is attached to the endoscope. In these embodiments the container is substantially similar to the containers of the above embodiments except that the air and water ports are provided below the base of the receptacle. The inlet aperture is still provided proximate the top of the receptacle and the outlet aperture is provided proximate the base of the receptacle and, as such, in these embodiments the first fluid conduit is substantially longer than the second fluid conduit. In these embodiments, however, it is necessary to incorporate one or more valves to control the flow of fluid into and out of the container during use, thereby making the design and manufacture of the container more complex and more expensive.

FIGS. 21 to 25 show a container 301 according to a fourth preferred embodiment of the present invention. The container 301 comprises a receptacle 306 and a connector or fluid conduit module 331.

The receptacle 306 has a first end wall or base 320 and an opposing second end wall or top 322. In this embodiment the receptacle 306 is substantially cuboidal and defines an internal volume of the receptacle 306 for containing sterile water. An opening 327 is provided in the top 322 of the receptacle 306 and a neck 328 extends upwards around the opening 326. The opening is offset from a central vertical axis of the receptacle 306.

The fluid conduit module 331 comprises a substantially rigid main body 333 made of a suitable plastics material. In some embodiments the main body 333 is made from an elastomeric material. The main body 333 has a generally L-shaped vertical cross-section. A first end 335 of the main body 333 includes a female air port 308 for connection to the air line of an endoscope 311 and a female water port 310 for connection to the water line of the endoscope 311, as described above.

A second end 337 of the main body 333 is configured to be engaged with the opening 327 of the receptacle 306. In this embodiment, an end portion 339 of the main body 333 is sized such that there is a push fit or interference fit of this end portion 339 into the opening 327. A flange or projecting ring 341 extends outwards around the main body 333 proximate the second end 337. When the end portion 339 is pushed into the opening 327, the flange 341 contacts an upper edge of the neck 328 around the opening thereby limiting the extent to which the main body 333 may be pushed into the receptacle 306.

In preferred embodiments a collar 343 is provided to secure the main body 333 to the receptacle 306. The collar 343 comprises a circular wall 345 having a lip 347 extending radially inwardly around a first end of the wall 345. Complementary screw threads are provided on an external or outwardly facing surface of the neck 328 and an internal or inwardly facing surface of the collar wall 345. As the collar 343 is screwed onto the receptacle 306, the flange 341 is gripped between the upper edge of the neck 328 and the lip 347 of the collar 343, thereby securing the fluid conduit module 331 to the receptacle 306.

In other embodiments the fluid conduit module 331 may be secured to the receptacle 306 by interengaging retaining means, similar to those described above in relation to embodiments 1 to 3.

Figure 25:
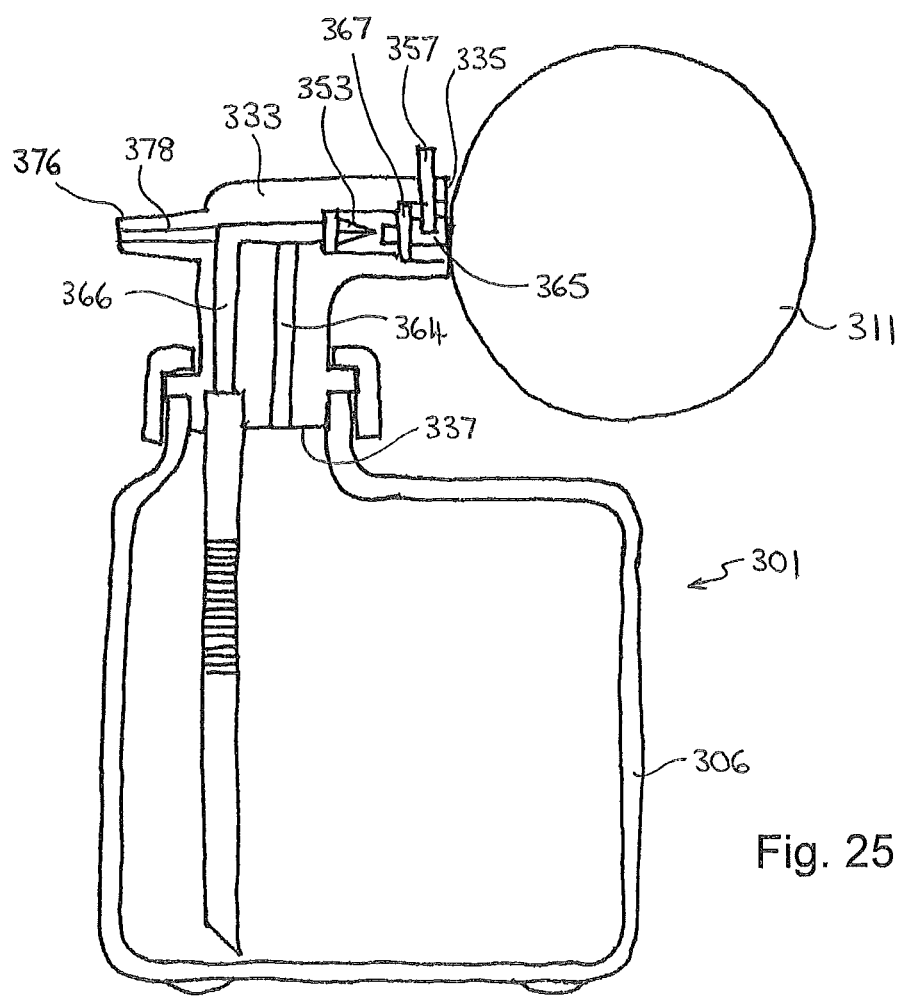
FIG. 25 is cross-sectional view showing the container of FIG. 21 connected to an endoscope.

A first fluid conduit or passageway 364 extends through the main body 333 from the air port 308 to the second end 337 of the main body 333. A second fluid conduit or passageway 366 extends through the main body 333 from the water port 310 to the second end 337 of the main body 333, as shown in FIG. 25.

Due to the shape of the main body 333 each of the first and second fluid conduits 364, 366 turns through about 90° between the first and second ends 335, 337 of the main body 333. In a preferred embodiment the first and second ends 335, 337 of the main body 333 are perpendicular to each other.

A tube 349 extends from the second end 337 of the main body 333 such that the tube 349 is in fluid connection and aligned with the second fluid conduit 366. When the fluid conduit module 331 is connected to the receptacle 306, the tube 349 extends downwards into the internal volume of the receptacle 306. The length of the tube 349 is such that a free end 351 of the tube 349 is located proximate the base 320 of the receptacle 306 when the main body 333 is fully seated in the opening 327. In some embodiments it may be desirable if at least a portion of the tube 349 is flexible to avoid kinks forming in the tube 349 that would block the flow of fluid along the tube.

In other embodiments the receptacle 306 may include an integrally formed fluid passageway (not shown) in place of the tube 349. The fluid passageway is preferably arranged such that a first open end of the passageway is positioned proximate the base of the receptacle. A second end of the passageway is located such that, when the fluid conduit module is inserted into the opening 327 in the receptacle 306, the second fluid conduit 366 aligns with and forms a fluid connection with the passageway.

In preferred embodiments of the fluid conduit module 331 a duckbill valve 353 is positioned in the second fluid conduit 366 to prevent contaminated water flowing from the water line of the endoscope 311 back into the receptacle 306.

The fluid conduit module 331 further comprises an auxiliary port 376 for connection to an additional source of gas, such as a source of carbon dioxide (not shown). The auxiliary port 376 comprises an inlet tube 378 that projects from the main body 333. A distal end 380 of the inlet tube 378 is adapted for connection to a source of carbon dioxide as typically used in an endoscopy procedure. The inlet tube 378 is in fluid connection with the first fluid conduit 364 such that either air or carbon dioxide may be used to pump water from the receptacle 306 when required.

The size and shape of the receptacle 306 and fluid conduit module 331 are such that the first end 335 of the main body 333 and the air and water ports 308, 310 lie directly above the centre of gravity of the container 301, i.e. the ports 308, 310 lie in the same vertical plane as the centre of gravity. Furthermore, the geometry of the container 301 is preferably such that, as the amount of water within the receptacle 306 varies, the centre of gravity shifts vertically but does not move horizontally. This arrangement means that, when the container 301 is connected to the endoscope 311, the receptacle 306 is suspended directly below the endoscope 311 and minimal twisting or bending forces are applied to the male air and water ports of the endoscope 311 due to the weight of the container 301.

To ensure that the fluid conduit module 331 is attached to the receptacle 306 in the correct orientation, the end portion 339 of the main body 333 and the neck 328 preferably include complementary alignment features so that the end portion 339 can only be inserted into the neck 328 in one orientation. In the embodiment illustrated in FIG. 24 the neck 328 has a horizontal cross-sectional shape in the form of a truncated circle, such that the neck is substantially circular with a part of the neck having a planar surface. The end portion 339 of the main body 333 has a similar cross-sectional shape (not shown) such that the pair of planar surfaces form alignment features preventing a user positioning the fluid conduit module 331 incorrectly with respect to the receptacle 306.

One advantage of this embodiment of the container 301 is that only one opening is formed in the receptacle 306, rather than the two openings of the previous embodiments. This single opening is used to fill the receptacle with water, as well as providing the point of attachment for the fluid conduit module. This makes the receptacle easier and cheaper to manufacture.

Figure 22:
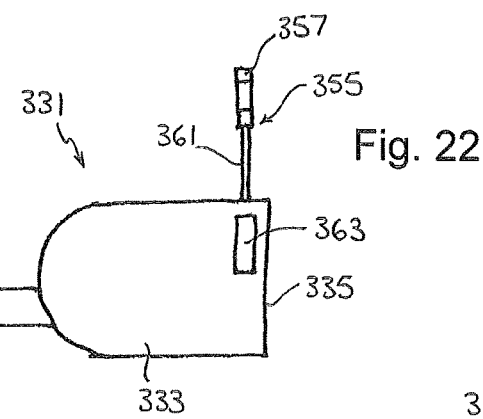
FIG. 22 is a view from above of the fluid conduit module of the container of FIG. 21.
Figure 23:
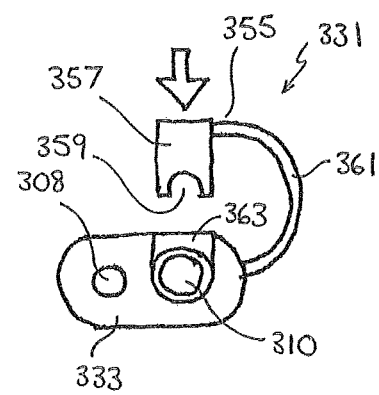
FIG. 23 is a view from one end of the fluid conduit module of the container of FIG. 21.
Figure 21:
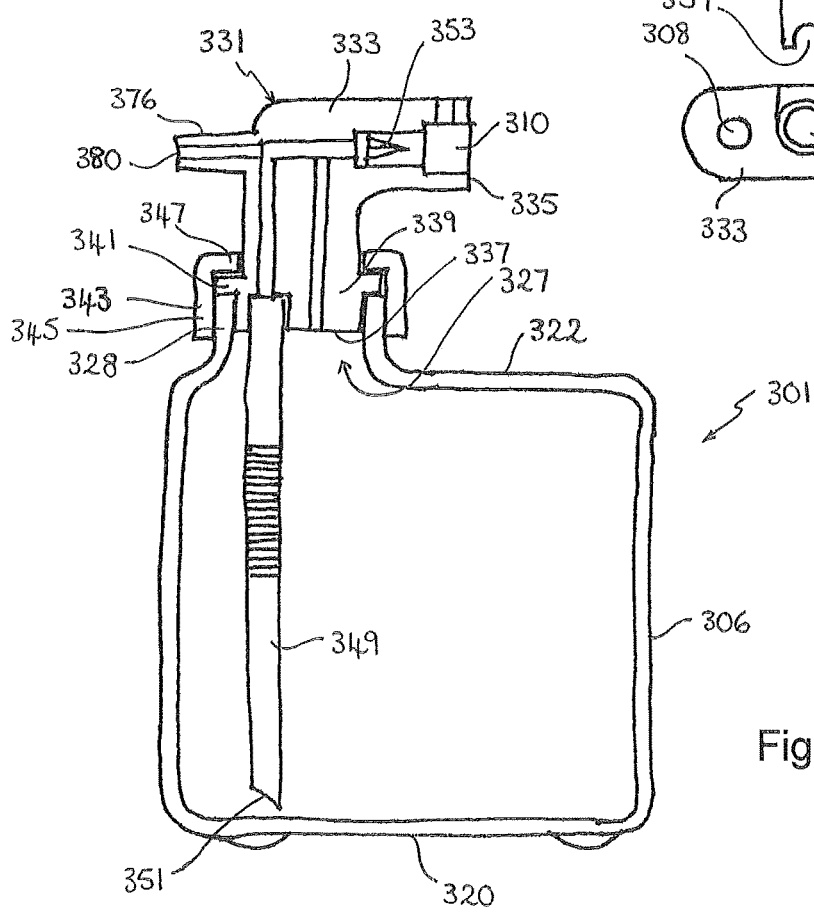
FIG. 21 is a cross-sectional view of a container for sterile water, comprising a receptacle and a fluid conduit module, according to a fourth preferred embodiment of the present invention.
Figure 24:
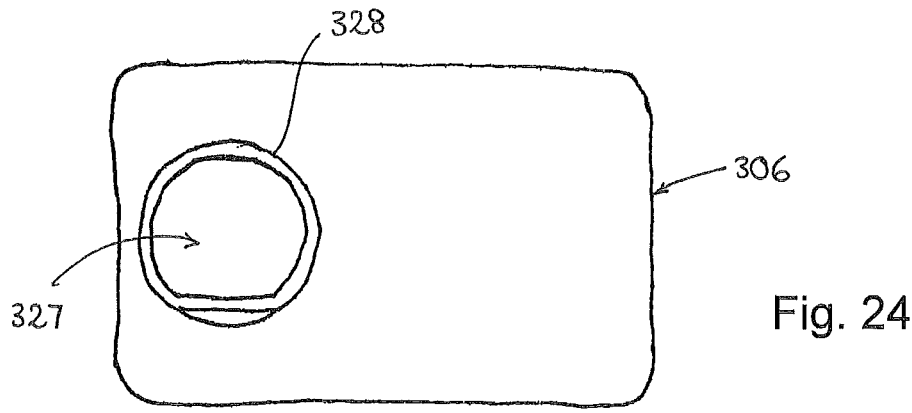
FIG. 24 is a view from above of the receptacle of the container of FIG. 21.

As shown in FIGS. 22, 23 and 25, the fluid conduit module 331 further comprises securing means 355 for fastening the container 301 to the male ports of the endoscope 311. In this embodiment the securing means 355 comprises a generally rectangular retaining plate 357 having a cut-out or notch 359 in one side. The retaining plate 357 is connected to the main body 333 of the fluid conduit module 331 proximate the first end 335 by means of a flexible strap 361.

The main body 333 has a channel 363 extending from a surface of the main body 333 to the water port 310 for receiving the retaining plate 357. The channel 363 has a rectangular cross-sectional shape and is sized such that there is an interference fit of the retaining plate 357 within the channel 363.

As illustrated in FIG. 25, the male water port on the endoscope 311 comprises a spigot 365 having a projecting rim 367 or raised engagement lugs that extend outwards around the spigot. As such, the diameter of the rim 367 is greater than the diameter of the spigot 365. The diameter of the female water port 310 of the fluid conduit module 331 is sized such that there is a push fit of the rim 367 into the port 310.

Once the water port 310 is fully engaged with the spigot 365 and rim 367, the retaining plate 357 is inserted into the channel 363. The location of the channel 363 relative to the spigot 365 is such that the retaining plate 357 contacts the spigot 365 behind the rim 367, i.e. between the rim 367 and the body of the endoscope 311. The notch 359 in the retaining plate 357 is preferably complementary to the shape of the spigot 365, and in this example the notch 359 has a semi-circular shape having a radius substantially the same as the radius of the spigot 365 and smaller than the radius of the rim 367. Inserting the retaining plate 357 into the channel 363, therefore, securely fastens the container 301 to the endoscope 311.

Although in this example the securing means 355 comprises a retaining plate 357, it will be appreciated that in other embodiments the securing means 355 may comprise other features for securing the fluid conduit module 331 to the male air or water port of the endoscope 311. The securing means 355 may comprise, for example, a cam member or a clamping mechanism.

The containers of the above embodiments are preferably made to be disposable, however, in other embodiments the container may be made out of a material which is sterilisable by steam or other means so that the container is reusable.

The container of the present invention, therefore, provides an improved means for the supply of sterile water to an endoscope. By designing the container such that the container is attached directly to the air and water ports of the endoscope, without requiring long lengths of flexible tubing, the complexity of the container is reduced and the likelihood of contamination of the water is also reduced.

The invention claimed is:
1. A container for storing sterile water for supply to an endoscope, the container comprising:
   a substantially rigid receptacle providing an internal volume for storing said water, the receptacle having opposing first and second end walls, in use said first end wall forming a base of the receptacle and said second end wall forming a top of the receptacle such that a vertical axis of the receptacle extends substantially perpendicular to the first and second end walls, and an aperture being provided in the receptacle;
   a connector comprising a substantially rigid main body, a first end of the main body being a first end of the connector and a second end of the main body arranged to be engaged with and removed from the aperture of the receptacle;
   a first port for connection to an air line of an endoscope and a second port for connection to a water line of an endoscope, the first and second ports being provided in said first end of the connector;
   a first fluid conduit formed in the main body of the connector and extending between the first port and said second end; and a second fluid conduit formed in the main body of the connector and extending between the second port and said second end, wherein, the aperture is offset from said vertical axis of the receptacle and, in use, the first and second ports are located in a fixed position with respect to the receptacle such that the first end of the connector lies in the same vertical plane as the centre of gravity of the container when the receptacle is filled with water.

2. A container as claimed in claim 1, wherein the first and second fluid conduits are substantially rigid.

3. A container as claimed in claim 1, wherein the first and second ports are located at a fixed distance above said top of the receptacle.

4. A container as claimed in claim 1, wherein the shape of the container is such that said centre of gravity remains in the same vertical plane, independent of the volume of water within the container.

5. A container as claimed in claim 1, wherein the second end wall includes an opening for filling the receptacle with sterile water.

6. A container as claimed in claim 1, wherein the aperture is provided in the second end wall of the receptacle.

7. A container as claimed in claim 1, wherein the first and second ends of the main body of the connector are substantially perpendicular to each other.

8. A container as claimed in claim 1, the container comprising a third port for connection to a source of gas and a third fluid conduit extending between the third port and the first fluid conduit.

9. A container as claimed in claim 1, wherein the receptacle comprises a neck portion that extends around the aperture, and a flange extends outwards around the main body of the connector at a distance from the second end, the flange being arranged to contact an upper edge of said neck when the second end of the main body is fully engaged with the aperture of the receptacle.

10. A container as claimed in claim 1, wherein the container further comprises a collar for securing the connector to the receptacle.

11. A container as claimed in claim 1, wherein the connector is made from an elastomeric material.

12. An assembly comprising a container for storing sterile water and an endoscope, the container being as claimed in claim 1, and wherein the container is solely suspended from the endoscope.

13. An assembly as claimed in claim 12, wherein the receptacle of the container is suspended below the endoscope.

14. A container as claimed in claim 1, further comprising a tube extending from the second end of the main body of the connector and being in fluid communication with the second fluid conduit.

15. A container as claimed in claim 14, wherein an end of the tube is disposed proximate the base of the receptacle when the connector is seated in the aperture.

16. A container as claimed in claim 14, wherein at least a portion of the tube is flexible.

17. A container as claimed in claim 1, wherein the receptacle includes an integrally formed fluid passageway, a first end of the passageway positioned proximate the base of the receptacle and a second end of the passageway positioned such that the second fluid conduit forms a fluid connection with the passageway.

* * * * *